United States Patent
Müller et al.

(10) Patent No.: US 8,124,813 B2
(45) Date of Patent: Feb. 28, 2012

(54) METHOD OF PRODUCING 2-PHENOXYACETALS AND THE CORRESPONDING 2-PHENOXY-CARBALDEHYDES THEREFROM

(75) Inventors: Thomas-Norbert Müller, Monheim (DE); Michael Dockner, Köln (DE)

(73) Assignee: SALTIGO GmbH, Langenfeld (DE)

( * ) Notice: Subject to any disclaimer, the term of this patent is extended or adjusted under 35 U.S.C. 154(b) by 20 days.

(21) Appl. No.: 12/665,066

(22) PCT Filed: Jun. 11, 2008

(86) PCT No.: PCT/EP2008/057303
§ 371 (c)(1),
(2), (4) Date: Jun. 23, 2010

(87) PCT Pub. No.: WO2009/000651
PCT Pub. Date: Dec. 31, 2008

(65) Prior Publication Data
US 2010/0286449 A1    Nov. 11, 2010

(30) Foreign Application Priority Data

Jun. 22, 2007 (DE) .................. 10 2007 028 925
Oct. 31, 2007 (DE) .................. 10 2007 052 313

(51) Int. Cl.
*C07C 43/315* (2006.01)
*C07C 45/42* (2006.01)
*C07C 41/50* (2006.01)

(52) U.S. Cl. ............. 568/592; 568/435; 568/442
(58) Field of Classification Search ........... 568/435, 568/442, 592
See application file for complete search history.

(56) References Cited

FOREIGN PATENT DOCUMENTS

| EP | 1564201 | | 8/2005 |
|----|---------|---|--------|
| JP | 60064941 | * | 4/1985 |
| JP | 2002-255905 | | 9/2002 |

OTHER PUBLICATIONS

Chioccara et al. New benzoxazine and benzothiazine cyanine dyes. Tetrahedron Letters, 1975, VOl. 10, 81-814. HCAPLUS Document No. 83:81176.*
Chiocarra et al. Some New Aspects on the Chemistry of 1,4-Benzoxazines. Journal of Heterocyclic Chemistry, 1985, vol. 22, 1021-1023.*
Bischoff, Chem. Ber. 1900, 33, 1603-1611.
Harfenist, J. Org. Chem. 1971, 36, 1171-1175.
Kawamatsu, Chem. Pharm. Bull. 1984, 32, 2267-2278.
Kwiecien, Polish J. Chem. 2004, 78, 249-254; Synth. Commun. 2005, 35, 2223-2250.
Paradisi/Scorrano, J. Org. Chem. 1983, 48, 3022-3026.
Seguchi, Yukagaku 1982, 31, 609-611.
Yi, Bull. Korean Chem. Soc. 2004, 25, 1003-1008.

* cited by examiner

*Primary Examiner* — Sikarl Witherspoon
(74) *Attorney, Agent, or Firm* — Michael A. Miller

(57) ABSTRACT

The invention relates to a novel process for preparing 2-phenoxyacetals and the corresponding 2-phenoxycarbaldehydes. These compounds are important intermediates for the preparation of active pharmaceutical ingredients.

4 Claims, No Drawings

METHOD OF PRODUCING 2-PHENOXYACETALS AND THE CORRESPONDING 2-PHENOXY-CARBALDEHYDES THEREFROM

The invention relates to a novel process for preparing 2-phenoxyacetals and the corresponding 2-phenoxycarbaldehydes. These compounds are important intermediates for the preparation of active pharmaceutical ingredients.

The only route to 2-phenoxyacetals described to date includes, as a key step, a Rosenmund reaction to prepare the aldehyde (FIG. 1). The acid chloride required for that purpose is obtainable by reaction of an α-halocarboxylic ester with the appropriate phenoxide, followed by a hydrolysis of the 2-phenoxy ester formed and subsequent treatment with thionyl chloride. The corresponding acetal is prepared by treating the aldehyde with methanol in the presence of catalytic amounts of acid. In this way, primarily aromatic compounds with electron-rich substituents (R=OMe, alkyl) were prepared [Kwiecien, *Polish J. Chem.* 2004, 78, 249-254; *Synth. Commun.* 2005, 35, 2223-2250]. One disadvantage of this method is the very laborious 5-stage synthesis route.

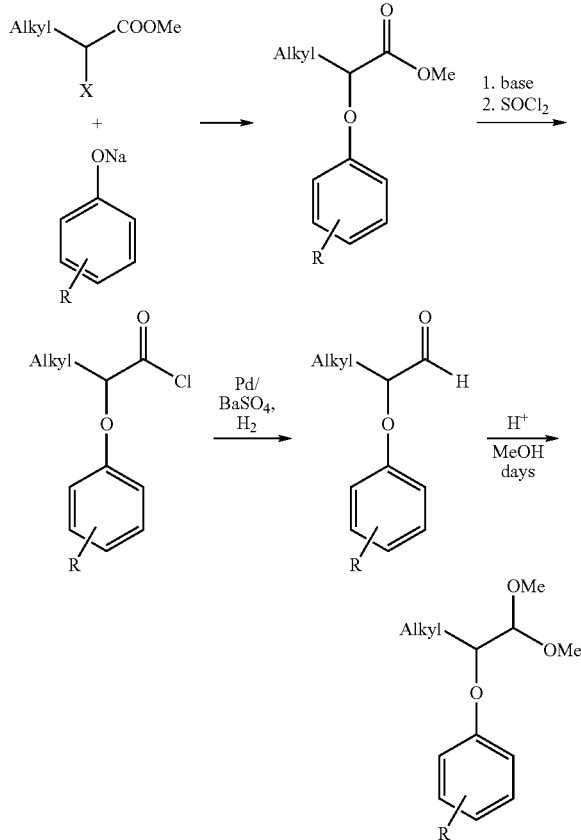

Figure 1 Preparation of hydroxyacetals according to Kwiecien.

2-Phenoxycarbonyl compounds with electron-deficient substituents are synthesized from the corresponding phenoxides and α-halogenated carbonyl compounds under much more severe conditions. For instance, high temperatures of 190-200° C. [Bischoff, *Chem. Ber.* 1900, 33, 1603-1611] or long reaction times [Harfenist, *J. Org. Chem.* 1971, 36, 1171-1175] are needed for the reaction. One variant for the etherification includes the deprotonation of the phenol with sodium hydride (FIG. 2). A disadvantage is the self-ignitability of sodium hydride and the associated need for safety measures. In order to obtain the desired carbaldehyde, it is first necessary to reduce the carboxylic acid obtained by hydrolyzing the ester to the alcohol, which is then oxidized to the target product. [Yi, *Bull. Korean Chem. Soc.* 2004, 25, 1003-1008]. A further disadvantage of this method is the long synthesis route and the associated low yield (32% over 5 stages).

Figure 2 Preparation of 2-carboxyaldehydes with electron-deficient substituents from the corresponding phenols according to Yi.

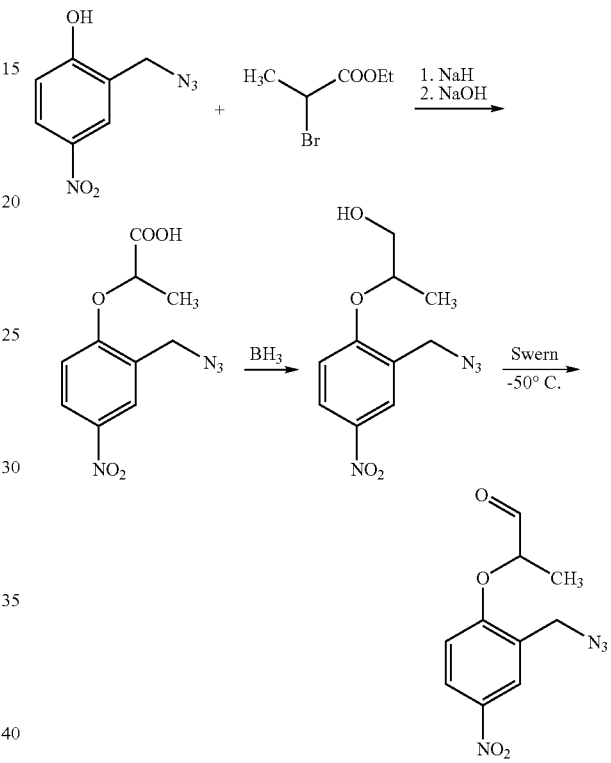

Aryl alkyl ethers with electron-deficient substituents are also prepared by reaction of aliphatic alcohols with the appropriate aryl halides (FIG. 3).

FIG. 3
Preparation of aryl alkylethers in the manner of a nucleophilic aromatic substitution ($S_NAr$).

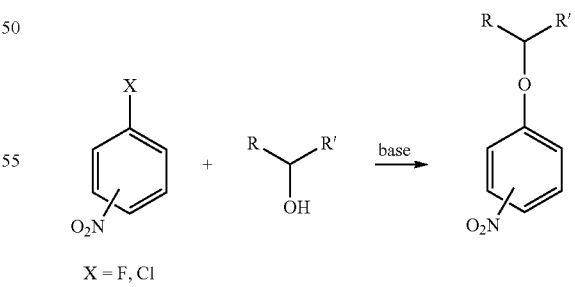

Typically, the alcohol is reacted directly as the alkali metal salt with the aryl fluoride or chloride, or is obtained in situ by addition of alkali metal hydrides or strong bases such as alkali metal hexamethyldisilazanes or alkali metal tert-butoxides. The use of alkali metal hydrides on a large scale is undesirable owing to their extremely high reactivity with water and the difficulty of handling them, and constitutes a great safety risk.

A further possibility is the use of a biphasic system, in which alcohol and aryl halide are dissolved in a water-immiscible solvent such as toluene, and the base required to deprotonate the nucleophile is present in an aqueous solution. Mediators used are phase transfer catalysts, typically quaternary ammonium halides.

However, the use of chloroaromatics leads to greatly varying yields owing to undesired side reactions of the aromatic starting material. For instance, in the case of selection of unsuitable reaction conditions, for example, the nitrophenols are formed as a secondary component from chloronitrobenzenes on a large scale.

Owing to their higher reactivity, aryl fluorides can be reacted with primary, secondary and tertiary alkoxides as nucleophiles [example of the reaction with tertiary alcohols: EP1564201A1]. According to the literature, the reaction of aryl chlorides with tertiary alcohols succeeds either only to a very small degree or not at all [Paradisi/Scorrano, *J. Org. Chem.* 1983, 48, 3022-3026; Seguchi, *Yukagaku* 1982, 31, 609-611]. There are only few examples of the reaction of aryl chlorides with unfunctionalized secondary alkoxides. One reaction is shown by way of example in FIG. 4 [Bansho, JP 2002-255905]. The yield was 86%.

Figure 4 Example of the preparation of aryl alkyl ethers with a secondary alcohol as the nucleophile.

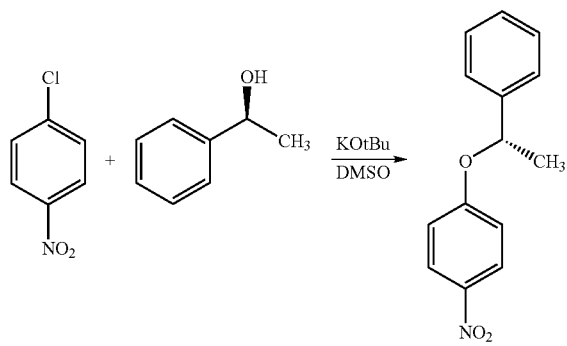

For the preparation of an aryl alkyl ether with a carbonyl functionality protected as the acetal in the side chain by nucleophilic substitution (FIG. 5), there is only one example in the literature [Kawamatsu, *Chem. Pharm. Bull.* 1984, 32, 2267-2278]. In this case, the primary alcohol shown below was reacted with 4-fluoronitrobenzene, which is significantly more reactive than the chlorine derivative. The desired product was obtained in 87% yield. A problem here is again the use of sodium hydride as a base and the associated complex measures for safe handling of this substance.

Figure 5 Preparation of aryl alkyl ethers by S$_N$Ar in the presence of acetal functionalities

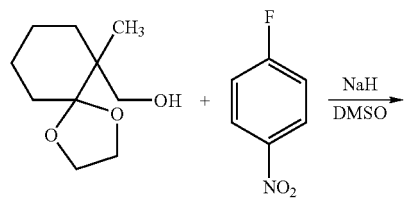

-continued

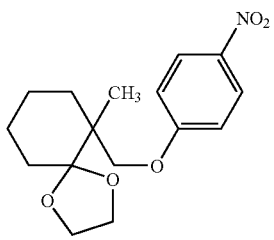

It was an object of the present invention to provide a novel, more economically viable process for preparing 2-phenoxyacetals and the corresponding 2-phenoxycarbaldehydes with improved yield.

In the present invention, it is possible to reduce the synthesis route to the 2-phenoxyacetals from five or six steps to one step (FIG. 6). The 2-hydroxyacetals required for that purpose are readily available in industrial amounts. The overall yield proceeding from the aldehyde has been enhanced from 31% to 55% compared to the method of Yi (FIG. 5). Moreover, synthesis operations which are problematic on the industrial scale, such as a Rosenmund reaction or a Swern oxidation, are avoided. The reaction of 4-chloronitrobenzene with secondary alcohols has been described to date only for unfunctionalized alcohols.

Figure 6 Inventive synthesis of 2-phenoxyacetals by nucleophilic aromatic substitution.

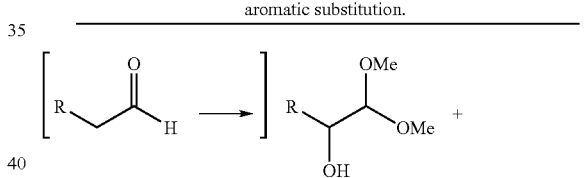

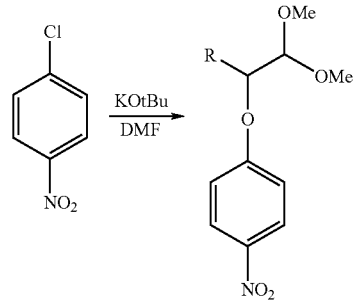

90-95%

A process has been found in which electron-deficient fluoro- and chloroaromatics can be reacted with 2-hydroxyacetals, 2-phenoxyacetals, surprisingly under mild conditions. In this case, the alcohol derivative is deprotonated in the presence of a strong base and then reacted with the desired chloroaromatic.

The invention therefore provides a process for preparing 2-phenoxyacetals of the general formula (Ia)

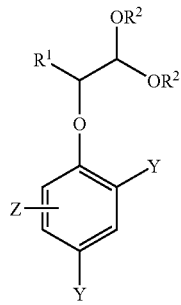

in which
R¹ is hydrogen, a branched or unbranched $C_1$-$C_{12}$-alkyl radical, an electron-deficient $C_5$-$C_6$-aryl or heteroaryl radical which is unsubstituted or substituted by halogen, an —$NO_2$, —CN, —$CF_3$ or acyl group or a branched or unbranched alkyl group, and
R² is a branched or unbranched $C_1$-$C_5$-alkyl radical or the two R² radicals are bonded to one another directly or via a $C_1$-$C_4$ unit,
Y one Y is always hydrogen and the other Y is an —$NO_2$, —CN or —$CF_3$ radical or fluorine or chlorine, or the two Y radicals are each independently an $NO_2$, CN or $CF_3$ radical or fluorine or chlorine,
Z is hydrogen or an —$NO_2$ radical or branched or unbranched $C_1$-$C_6$-alkyl radical or acyl radical,
by reacting a 2-hydroxyacetal compound of the general formula (II)

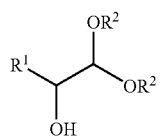

in which
R¹ and R² are each as defined for formula (Ia)
with a substituted aromatic of the general formula (III)

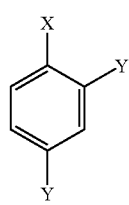

in which
Y is as defined for formula (I) and
X is fluorine, chlorine, bromine or an $NO_2$ group
in the presence of a base.

The base used may be an alkali metal alkoxide such as sodium or potassium methoxide-ethoxide or tert-butoxide, preferably potassium tert-butoxide, or solid alkali metal hydroxide such as sodium or potassium hydroxide in combination with solid alkali metal carbonate such as sodium, lithium or potassium carbonate, preferably solid potassium carbonate.

The specific procedure is to initially charge, in anhydrous solvents, for example dimethyl sulfoxide (DMSO), dimethylacetamide (DMAc), N-methylpyrrolidone (NMP), tetrahydrofuran (THF) and especially dimethylformamide (DMF), an alkali metal alkoxide in an amount of 1.1 to 1.2 equivalents, for example potassium tert-butoxide as a 10-50% and especially 20-30% solution, and to meter thereto a 2-hydroxyacetal of the formula (I), e.g. 1,1-dimethoxy-2-hexanol (1.0 equivalent). Subsequently, 1.05 to 1.2 equivalents of the substituted aromatic of the formula (II), for example 4-chloronitrobenzene as a 30% solution in a solvent such as DMF, are metered in over a period of 0.25 to 2 hours, especially 0.5 to 1 hour. Subsequently, stirring is continued at 30 to 60° C., especially 40° C., for another 1 to 6 hours. After the salts have been washed out, the solvent can then be removed, for example by distillation. The yields are typically 90-95% and the purity is more than 90%.

In addition to DMF, the solvent used may also be a mixture of DMF with toluene, chlorobenzene or xylene. Typically, the DMF content is 40% by weight or higher.

The base used may preferably be solid alkali metal hydroxide, e.g. solid potassium hydroxide or sodium hydroxide, in combination with solid alkali metal carbonate. In this case, preference is given to using 1 to 2 equivalents and particular preference to using 1.3 to 1.6 equivalents of the hydroxide in solid form. The alkali metal hydroxide/alkali metal carbonate ratio may be varied between 1:1 and 10:1. The solid alkali metal hydroxide used is preferably solid potassium hydroxide, and the solid alkali metal carbonate used is preferably solid potassium carbonate.

In the case of use of solid potassium hydroxide or sodium hydroxide in combination with solid potassium carbonate, the process solvent used is typically toluene or chlorobenzene, but other halogenated or nonhalogenated aromatic or aliphatic hydrocarbons may also be useful as solvents. In addition, the reaction can also be performed in the presence of 0.1 to 1.0 equivalent of a polar aprotic solvent. In this case, typically dimethylacetamide or N-methylpyrrolidone is used. The procedure is normally to mix all reagents and solvents and to heat the reaction mixture to the desired temperature. The reaction is typically performed at temperatures between 40 and 100° C., more preferably at temperatures between 60 and 80° C. The reaction time is typically between 4 and 14 hours. For workup, water is typically added to dissolve the salts, and the organic phase is also washed repeatedly with water.

In the 2-phenoxyacetals prepared by the process according to the invention, R¹ is preferably a $C_4$-alkyl or phenyl radical. R¹ may, though, also be a $C_5$-$C_6$-aryl or heteroaryl radical substituted, for example, by a halogen, a —CN, —$NO_2$, —$CF_3$, acyl or alkyl group, for example ethyl or isopropyl. Unsubstituted aryl radicals such as phenyl, or branched and unbranched $C_1$-$C_{12}$-alkyl radicals, are also possible.

R² may be a branched or unbranched $C_1$-$C_{12}$-alkyl radical, for example methoxide, ethoxide, propoxide, isopropoxide, sec- or tert-butoxide, or an amyl radical. The two R² radicals may, though, also be joined directly to one another or via a $C_1$-$C_4$, unit. One example thereof is, for example, a glycol radical.

R² is especially a methyl or ethyl group, and the compounds of the general formula (II) are thus a 2-aryloxy dimethyl acetal or a 2-aryloxy diethyl acetal.

Y may be in the ortho or para position on substituted aromatics, i.e. a Y in formula (I) is always hydrogen. The other Y is preferably an —NO$_2$ group. Otherwise, Y may also be a CN or CF$_3$ group or fluorine or chlorine. Y may also, either in the ortho position or in the para position, in each case independently be an NO$_2$, CN or CF$_3$ group, or else fluorine or chlorine.

Z in formula (I) and (III) may be hydrogen or a branched or unbranched C$_1$-C$_6$-alkyl radical, e.g. a methyl, ethyl or isopropyl radical. Z in formula (I) and (II) is preferably hydrogen.

By acidic hydrolysis, it is easily possible to convert the 2-phenoxyacetals prepared in accordance with the invention to the corresponding 2-phenoxycarbaldehydes. The hydrolysis is preferably performed immediately after the preparation of the 2-phenoxyacetals by adding water and an inorganic (37% HCl) or organic acid such as formic acid to the reaction solution. The preparation of the corresponding 2-phenoxycarbaldehydes from the 2-phenoxyacetals obtained in accordance with the invention therefore likewise forms part of the subject-matter of this invention.

The 2-phenoxyacetals obtained by this route and the carbaldehydes thereof are starting materials of economic interest for 2-alkyl-5-nitrobenzofurans, which find use as precursors of pharmaceutical products.

The 2-phenoxyacetals of the corresponding 2-phenoxycarbaldehydes therefore likewise form part of the subject-matter of the invention. A preferred 2-phenoxyacetal is 1,1-dimethoxy-2-(4-nitrophenoxy)hexane.

EXAMPLES

Preparation of
1,1-dimethoxy-2-(4-nitrophenoxy)hexane from
4-chloronitrobenzene

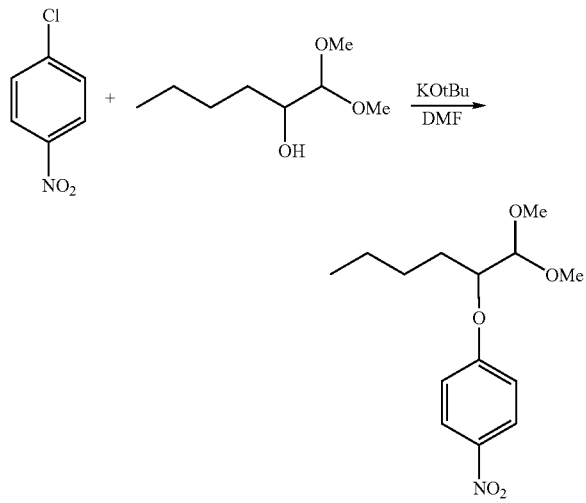

A 1 l flat-flange vessel was initially charged at room temperature with 1.1 equivalents of potassium tert-butoxide as a 30% solution in DMF, and then 1.0 equivalent of 1,1-dimethoxy-2-hexanol was metered in within 15 minutes. The mixture was stirred for 15 minutes and then, at 25° C., 1.1 equivalents of 4-chloronitrobenzene were metered in as a 30% solution (by weight) in DMF within 1 hour. The mixture was subsequently stirred at a temperature of 40° C. between a further 4 hours. The reaction mixture was subsequently cooled to 15° C. and extracted with the same volume of methyl tert-butyl ether. Subsequently, the combined organic phases were washed twice with a volume of water equal to one third of the volume of the organic phase each time, and the solvent was removed under reduced pressure. The desired product was obtained as a brown oil in 93% purity and 95% yield.

Preparation of
1,1-dimethoxy-2-(4-nitrophenoxy)hexane from
4-fluoronitrobenzene

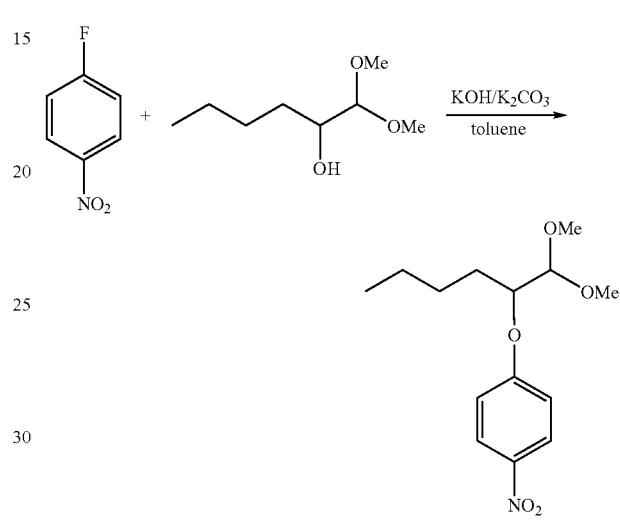

A 1 l flat-flange vessel was initially charged with 1 equivalent of 1,1-dimethoxy-2-hexanol as a 30% solution in toluene, and 1.05 equivalents of 4-fluoronitrobenzene were added. Subsequently, 0.33 equivalent of N-methylpyrrolidone, 0.12 equivalent of solid potassium carbonate and 1.5 equivalents of solid potassium hydroxide were added. The reaction mixture was heated to 80° C. with stirring for 7 hours. Subsequently, the mixture was cooled to 55° C. and water was added. The aqueous phase was removed and the organic phase was washed twice more with water. After the solvent had been removed, the product was obtained in 94% purity and 92% yield.

What is claimed is:

1. A process for preparing a compound of general formula (IA)

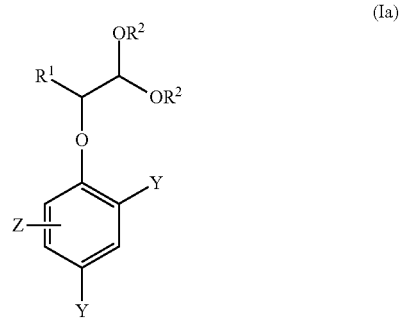

in which

- $R^1$ is hydrogen, a branched or unbranched $C_1$-$C_{12}$-alkyl radical, an electron-deficient $C_5$-$C_6$-arly or heteroaryl radical which is unsubstituted or substituted by halogen, an $NO_2$, —CN, —$CF_3$ or acyl group or a branched or unbranched alkyl group, and
- $R^2$ is a branched or unbranched $C_1$-$C_5$-alkyl radical or the two $R^2$ radicals are bonded to one another directly or via a $C_1$-$C_4$ unit,
- Y one Y is always hydrogen and the other Y is an —$NO_2$,—CN or —$CF_3$ radical or fluorine or chlorine, or the two Y radicals are each independently an $NO_2$, CN or $CF_3$ radical or fluorine or chlorine,
- Z is hydrogen or an —$NO_2$ radical or branched or unbranched $C_1$-$C_6$-alkyl radical or acyl radical, by reacting a 2-hydroxyacetal compound of the general formula (II)

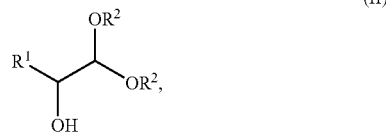

(II)

in which $R^1$ and $R^2$ are each as defined for formula (Ia)

with a substituted aromatic of the general formula (III)

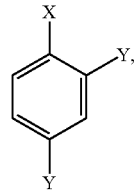

(III)

in which

Y is as defined for formula (I) and

X is fluorine, chlorine, bromine or an $NO_2$ group, in the presence of a base, characterized in that the reaction is performed in anhydrous dimethylformamide as a solvent.

2. The process as claimed in claim 1, characterized in that the 2-hydroxyacetal compound of the formula (II) is pretreated with an alkoxide before reaction with the substituted aromatic of the general formula (III).

3. The process as claimed in claim 1, characterized in that the base is an alkali metal alkoxide.

4. The process as claimed in claim 1 characterized in that the base is a solid alkali metal hydroxide in combination with solid alkali metal carbonate.

* * * * *